United States Patent
Ikemoto et al.

(10) Patent No.: US 7,927,874 B2
(45) Date of Patent: Apr. 19, 2011

(54) METHOD OF TRANSFERRING SUBSTANCE INTO CELL

(75) Inventors: Kazuto Ikemoto, Niigata (JP); Yusuke Okubo, Saitama (JP); Kanako Koike, Saitama (JP); Sayaka Aizawa, Saitama (JP); Ichiro Sakata, Saitama (JP); Takafumi Skai, Saitama (JP)

(73) Assignees: Mitsubishi Gas Chemical Company, Inc., Tokyo (JP); Saitama University, Saitama (JP)

( * ) Notice: Subject to any disclaimer, the term of this patent is extended or adjusted under 35 U.S.C. 154(b) by 0 days.

(21) Appl. No.: 12/227,405

(22) PCT Filed: May 16, 2007

(86) PCT No.: PCT/JP2007/060039
§ 371 (c)(1),
(2), (4) Date: Nov. 17, 2008

(87) PCT Pub. No.: WO2007/132891
PCT Pub. Date: Nov. 22, 2007

(65) Prior Publication Data
US 2009/0233367 A1     Sep. 17, 2009

(30) Foreign Application Priority Data

May 16, 2006   (JP) ................................. 2006-136851
May 16, 2006   (JP) ................................. 2006-136856

(51) Int. Cl.
*C12N 15/87* (2006.01)
(52) U.S. Cl. ......... 435/459; 435/461; 435/470; 435/471
(58) Field of Classification Search ........................ None
See application file for complete search history.

(56) References Cited

U.S. PATENT DOCUMENTS

| | | | |
|---|---|---|---|
| 4,945,050 | A | 7/1990 | Sanford et al. |
| 6,093,557 | A | 7/2000 | Pui et al. |
| 6,399,362 | B1 | 6/2002 | Pui et al. |
| 6,433,154 | B1 | 8/2002 | Ostrander et al. |
| 6,746,869 | B2 | 6/2004 | Pui et al. |

FOREIGN PATENT DOCUMENTS

WO     WO98/56894     12/1998

OTHER PUBLICATIONS

Okubo et al., "DNA Introduction into Living Cells by Water Droplet Impact with an Electrospray Process," *Angewandte Chemie* (International Edition), 2008, vol. 47, No. 8, pp. 1429-1431.
Chen et al., "A novel approach for introducing bio-materials into cells," *Journal of Nanoparticle Research*, 2000, vol. 2, pp. 133-139.
Ikemoto, "Gene introduction into cell by electrospray," The 52nd Meeting of the Japan Society of Applied Physics and Related Societies, *Extended Abstracts*, 2005, p. 1451.
First Office Action dated Jun. 9, 2010 corresponding (Chinese Application No. 2007/80022741.8), Chinese and English translation from the Republic of China Patent Office.
Second Office Action dated Dec. 6, 2010 corresponding (Chinese Application No. 2007/80022741.8), Chinese and English translation from the PRC Patent Office.

*Primary Examiner* — James S Ketter
(74) *Attorney, Agent, or Firm* — Fitch, Even, Tabin & Flannery (57) ABSTRACT

There is provided a method by which multiple types of substances desired to be transferred into cells can be continuously transferred into multiple types of cells by a convenient procedure, a cell in which the substance desired to be transferred into cells has been taken up by this method, and an apparatus for transferring a substance into cells by this method. The foregoing objects can be achieved by electrospraying cells with a liquid free from the substance to be transferred into cells while the cells are kept in contact with the substance to be transferred into cells, or first electrospraying cells with a liquid free from the substance to be transferred into cells and then bringing the cells into contact with the substance to be transferred into cells.

5 Claims, 5 Drawing Sheets

METHOD OF TRANSFERRING SUBSTANCE INTO CELL

CROSS-REFERENCE TO RELATED APPLICATIONS

This is a U.S. National Phase of International Application PCT/JP2007/060039, filed May 16, 2007, and claims the benefit of foreign priority under 35 U.S.C. §119 based on JP 2006-136851 and JP 2006-136856, filed May 16, 2006, the entire disclosures of which applications are hereby incorporated herein by reference.

TECHNICAL FIELD

The present invention relates to a method by which a substance to be transferred into cells can be continuously and conveniently transferred into cells; a cell into which a substance to be transferred into cells has been transferred by the above method; and an apparatus for transferring a substance to be transferred into cells by the above method. More specifically, the present invention relates to a method for transferring a substance into cells, which comprises, in order that a substance to be transferred into cells is allowed to be taken up into cells, electrospraying a liquid free from the substance to be transferred into cells to generate droplets, and spraying the droplets on cells in the presence of the substance to be transferred into cells, or first spraying the droplets on cells and then bringing the substance to be transferred into cells into contact with the cells; a cell into which the substance to be transferred into cells has been taken up by the above method; and an apparatus for transferring the substance into cells by the above method.

Methods for transferring genes such as DNA and RNA, proteins such as enzymes and antibodies, and chemical substances such as drugs into cells, cells obtained by these methods, and apparatuses utilizing these methods are useful measures in research and development in biotechnology-related areas such as medicine, pharmacy and agriculture as well as clinical settings such as gene therapies and targeting therapies against cancer cells.

BACKGROUND ART

Many methods and apparatuses have been developed for use in procedures in which substances desired to be transferred into cells are transferred into cells, particularly, gene recombination procedures in which genes such as DNA and RNA are introduced into cells.

For example, competent cells are often used for bacteria and yeasts which have cell walls containing peptide glucan, cellulose and the like (for example, refer to Non-Patent Document 1). This is a method in which cells are altered so as to easily take up substances, and then heat shock or the like is applied to the cells so as to allow the substance to be taken up. However, this method is problematic in that it is complex and time-consuming because conditions for culture of cells to be used must be strictly regulated, and cells must be frozen or treated with a solution containing metal ions without killing the cells (for example, refer to Non-Patent Documents 2 and 3).

Animal cells usually proliferate more slowly and have greatly different cell structures and cell membrane structures than bacteria and other microorganisms. Therefore, it is generally said to be difficult to transfer a substance into animal cells as compared with microorganisms, and very fine handling is required for animal cells. Therefore, transfer into animal cells of genes such as DNA and RNA or other substances to be transferred into cells cannot be made without difficulty.

Several methods targeting animal cells have been proposed. One example is a calcium phosphate method (for example, refer to Non-Patent Document 4). This is a method in which calcium phosphate particles containing DNA are made and allowed to be taken up via endocytosis. However, this method has drawbacks such that procedures are complex, and transfer efficiency is low. As a modification of this method, a method has been proposed in which substances are allowed to be taken up into cells using reagents such as cationic polymers and liposomes (for example, refer to Non-Patent Documents 5 and 6). However, this method is problematic in that very complex procedures are required to mix reagents with cells, and the reagents to be used are expensive. Furthermore, these reagents may exert a fatal action on cells depending on doses and can only be used within a limited range of concentrations.

In addition to these methods, methods in which viruses are utilized to transfer substances into cells are available (for example, refer to Non-Patent Document 7). However, complex purification procedures are required when viruses are used. Because of viruses, there is a risk that substances may be transferred into cells or tissues that are not targeted. Furthermore, because of viruses, biohazard risk must be considered.

Electroporation is a well-known method by which a substance to be transferred into cells is allowed to be taken up into cells (for example, refer to Patent Document 1). This is a method in which a high pulsed voltage is applied to a suspension containing a gene and a cell so as to allow the gene contained in the suspension to be taken up into the cell. This method is wide in application and high in gene transfer efficiency. However, since gene transfer efficiency has a proportional relationship with cell fatality rate, the transfer of substances cannot be carried out independently of cell fatality. Specifically, the method has drawbacks such that, if pulse conditions are inappropriate, not only targeted substances are hardly transferred into cells, but also cells may die. Furthermore, in order to prevent so-called towing which is electric discharge into a solution, electrical conductivity of the cell suspension must be reduced when a voltage is applied. For this purpose, procedures of isolating and washing cells with centrifugation or the like are required, during which cells may die.

Furthermore, a particle gun is used as a method for transferring a substance into cells (for example, refer to Patent Document 2). This is a method in which gene-carrying microparticles of gold, tungsten or the like are shot into cells. The substance to be transferred into cells is carried by microparticles so as to increase the whole mass, and is allowed to hit cells with high energy so as to penetrate through cell membranes. This method shows high transfer efficiency against cells hit by microparticles, but has drawbacks such that, when there are lots of cells, microparticles do not uniformly hit the cells, thereby making it difficult to increase the total transfer efficiency. Furthermore, this method also has drawbacks such that a procedure of attaching genes to microparticles or the like is required, and consumable materials such as microparticles for carrying substances and rupture discs for releasing pressure are expensive. Furthermore, there are also drawbacks such that an apparatus is bulky because a plasma explosion, an explosive or a compressed gas cylinder must be used to shoot microparticles, cells are scattered by the blast of gas, cells are easily damaged because particles remain in cells, particles are accumulated in cells after shooting is repeated, and so forth. The retention and accumulation of microparticles in cells are not desirable particularly for gene therapy because probability of cell death is increased. Furthermore, since sizes of microparticles to be used are from 0.5 to 3 µm, it is very difficult to apply this method to, for example, minute cells such as bacteria having a size of around 1 µm, although relatively large cells such as of plants and animals having a size of 10 to 100 µm have little problem.

Electrospray is used as a method for spraying a liquid at high speed. Electrospray is a method in which electric charges are collected at the tip of a spray tube by applying a high voltage to the tube, and a liquid is passed through the tube tip at which the electric charges have been accumulated, thereby allowing the liquid to be converted into minute charged droplets and sprayed on a target at high speed. This method has been used specifically as an ionization method in mass spectrometry (for example, refer to Non-Patent Documents 8 and 9).

As one of the particle gun techniques utilizing this electrospray, there is a method in which a high voltage is applied to a suspension containing particles through the tip of a capillary in order to spray them on cells (for example, refer to Patent Document 3). This method uses the electrospray in order to accelerate particles to which a substance to be transferred into cells is attached or a liquid containing the substance together with the particles. In either case, this method has a drawback such that the capillary tip may be clogged with particles because the suspension containing particles is used. Furthermore, like usual particle guns, the method has a drawback such that solids remain in cells. Furthermore, every time when the substance to be transferred into cells is changed, the procedure for carrying the substance must be done, although this is unnecessary when one type of a substance desired to be transferred into cells is to be transferred. Furthermore, the liquid transfer system for the suspension must be subjected to washing and replacement every time they are used, and problems of complex procedures and time-consumption still remain unsolved. Furthermore, since a suspension containing a substance to be transferred is sprayed, the inside of an apparatus may be contaminated. Furthermore, spark discharge is more likely to occur between the tube and cells as the amount of a solute contained in a spray solution is increased.

Under such circumstances of background art, provision of a method and an apparatus has been demanded in which a substance to be transferred into cells can be conveniently and continuously transferred into cells as it is without the need of attaching the substance to be transferred into cells to carriers such as particles, and in which multiple types of substances to be transferred into cells can be continuously transferred into multiple types of cells in a short time.

Patent Document 1: U.S. Pat. No. 4,945,050.
Patent Document 2: Japanese Patent No. 2606856.
Patent Document 3: U.S. Pat. No. 6,093,557.
Non-Patent Document 1: H. Inoue, H. Nojima, H. Okayama, Gene, 1990, vol. 96(1), p 23-28.
Non-Patent Document 2: J. Haensler, F. C. Szoka Jr, Bioconjugate Chem., 1993, vol. 4, p 374-379.
Non-Patent Document 3: P. L. Felgner, T. R. Gadek, M. Holm, R. Roman, H. W. Chan, M. Wenz, J. P. Northrop, G. M. Ringold, and M. Danielsen, 1147766570484_0.'); 1987, vol. 84(21), p 7413-7.
Non-Patent Document 4: F. L. Graham, A. J. Van Der Eb, Virology, 1973, vol. 52, p 446-467.
Non-Patent Document 5: J. Haensler, F. C. Szoka Jr, Bioconjugate Chem., 1993, vol. 4, p 374-379.

Non-Patent Document 6: P. L. Felgner, T. R. Gadek, M. Holm, R. Roman, H. W. Chan, M. Wenz, J. P. Northrop, G. M. Ringold, and M. Danielsen, 1147765309078_0.'); 1987, vol. 84(21), p 7413-7.
Non-Patent Document 7: D. Yu, T. Shioda, A. Kato, M. K. Hasan, Y. Sakai, Y. Nagai, 1147765309078_1.'); 1997, vol. 2(7), p 457-66.
Non-Patent Document 8: J. B. Fenn, M. Mann, C. K. Meng, S. F. Wong, C. M. Whitehouse, Science, 1989, vol. 246, p 64-71.
Non-Patent Document 9: Z. Takats, J. M. Wiseman, B. Gologan, R. G. Cooks, Science, 2004, vol. 306, p 471-473.

DISCLOSURE OF THE INVENTION

Problems to be Solved by the Invention

An object of the present invention is to provide a method for introduction into cells of a substance desired to be transferred into cells, for example, transferring a high molecular weight bioactive substance such as genes including DNA and RNA into cells, which can continuously and conveniently transfer the substance into cells without the need of a complex carrier-attaching procedure or a procedure of mixing with particles or the need of a procedure of washing and replacing a liquid transfer system each time a substance to be transferred is changed, and which can easily transfer different kinds of substances into cells of different specimens, as well as a cell obtained by this method, and an apparatus for transferring a substance into cells by this method.

Means for Solving the Problems

The present inventors have made intensive studies in order to achieve the foregoing object. As a result, they have unexpectedly found that droplets should be generated and brought into contact with cells by electrospraying a liquid containing no substance to be transferred into the cells when a substance to be transferred into cells is transferred into cells, and thereby multiple types of substances to be transferred into cells can be efficiently transferred into multiple types of cells. Thus, the present invention has been accomplished.

Specifically, the present invention relates to a method for transferring a substance into cells, which is characterized in that a liquid free from the substance to be transferred into cells is electrosprayed on cells, a cell obtained by this method, and an apparatus for transferring a substance into cells by this method, as described in the following items (1) to (9).

(1) A method for transferring a substance into cells, which comprises electrospraying a liquid free from the substance to be transferred into cells so that droplets are generated and brought into contact with cells, in order that the substance is transferred into the cells.

(2) The method for transferring a substance into cells according to the above item (1), wherein said droplets are brought into contact with cells that coexist with the substance to be transferred into cells.

(3) The method for transferring a substance into cells according to the above item (1), wherein said droplets are first brought into contact with cells, and then said cells are brought into contact with the substance to be transferred into cells.

(4) The method for transferring a substance into cells according to the above item (3), wherein said cells are brought into contact with the substance to be transferred into cells within 30 minutes or less after said droplets have been brought into contact with said cells.

(5) The method for transferring a substance into cells according to the above item (1), wherein a potential difference between the liquid and the cells is 0.1 kV to 100 kV.
(6) The method for transferring a substance into cells according to the above item (1), wherein the liquid which is electrosprayed is water that is free from the substance to be transferred into cells or an aqueous solution that is free from the substance to be transferred into cells.
(7) The method for transferring a substance into cells according to the above item (1), wherein the substance to be transferred into cells is a gene.
(8) A cell into which a substance to be transferred into cells has been transferred by the method according to any one of the above items (1) to (7).
(9) An apparatus for transferring a substance into cells by the method according to any one of the above items (1) to (7).

Effects of the Invention

According to the present invention, a substance desired to be transferred into cells, in particular, a gene can be transferred into cells without the need of complicated pretreatment. Specifically, a substance desired to be transferred can be directly transferred into cells without performing complex pretreatment procedures for previously attaching the substance to a carrier, and hence no carrier remains in cells. Furthermore, since no limitation is imposed on the present invention by carrier particle sizes, the present invention can be applied to small cells of submicrons to several microns such as bacteria.

Furthermore, the apparatus of the present invention does not require any expensive metal microparticles or rupture discs, but the cost per treatment is reduced. Furthermore, since there is no need of changing the liquid to be sprayed or the like, multiple types of genes can be continuously transferred into multiple types of cells in a short time. As a result, time required for procedures such as gene recombination can be significantly reduced as compared with conventional methods, and a large amount of specimens can be processed.

BEST MODE FOR CARRYING OUT THE INVENTION

Hereinafter, embodiments of the present invention will be explained in detail.

Cells used in the present invention are not particularly limited, but may be any of cells of animals, plants and microorganisms. Besides the cells, tissues, organs and organisms may be also included. It is also needless to say that reproductive cells such as eggs, sperms, pollens, spores and seeds can be targeted.

The present invention is effective particularly for animal cells. Animal cells are specifically defined as organisms belonging to the kingdom Animalia and those belonging to the protozoa based on the five kingdom system, and cells derived therefrom. The organisms belonging to the kingdom Animalia are multicellular organisms which are composed of eukaryotic cells, have no photosynthetic ability, and are heterotrophic. This kingdom includes Porifera, Coelenterata, Platyhelminthes, Aschelminthes, Annelida, Mollusca, Arthropoda, Chaetognatha, Echinodermata, Protochordata, and Vertebrata. Furthermore, protozoa are unicellular organisms which belong to the kingdom Protista, are composed of a eukaryotic cell, and are heterotrophic.

When cells such as bacteria, yeasts, filamentous fungi, archaea and plants, which have a cell wall, are used, it is expected that transfer efficiency is improved by using those with a damaged cell wall or those with a plasma membrane exposed by removing the cell wall. In the presence of a substance that generates the above-mentioned states, the spraying may be conducted. Specific examples of such cells include competent cells and cells whose walls have been weakened such as protoplasts, and these may be allowed to coexist with Ca ions, Li ions, Rb ions, Cs ions, Mg ions, Mn ions, Zn ions, cellulase, pectinase and others that are used to prepare these cells. Furthermore, they may be allowed to coexist with polymers such as polyethylenimine, polyallylamine, polyspermine, polyricin and polyethylene glycol, and surface active substances such as liposomes and micelles. To allow these substances to coexist, a method of previously adding them to a cell solution onto which spraying is conducted or a method of mixing them at the stage of spraying, may be suitably selected.

The present invention is characterized in that a liquid free from the substance to be transferred into cells are electrosprayed so that droplets are generated and brought into contact with cells in order that the substance is transferred into cells. More specifically, in order that the substance to be transferred into cells is taken up into cells, a liquid free from the substance to be transferred into cells is electrosprayed on cells whilst the cells are kept in contact with the substance to be transferred into cells, or a liquid free from the substance to be transferred into cells is first electrosprayed on cells, and then the cells are brought into contact with the substance to be transferred into cells.

Figure 1:
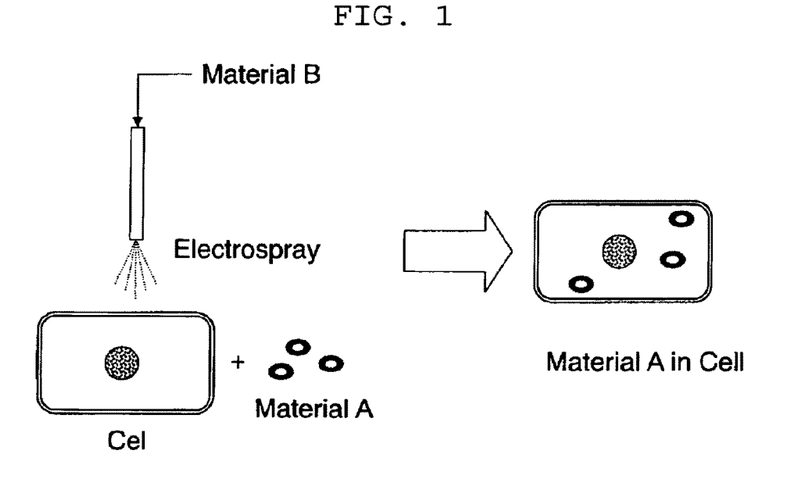
FIG. 1 is a schematic view showing a case in which electrospray is performed whilst cells are kept in contact with a substance to be transferred into cells.

The electrospray referred to in the present invention converts a liquid to droplets by allowing the liquid to pass through a fine tube tip to which a high voltage is applied, and jets minute liquid microparticles against target cells at a high speed due to repulsion of electric charge on droplet surfaces. FIG. 1 shows an embodiment of the present invention in which a liquid free from the substance to be transferred into cells is electrosprayed on cells whilst the cells are brought into contact with the substance to be transferred into cells.

In FIG. 1, cells (Cell) coexist with the substance (Material A) to be transferred into cells. A liquid (Material B) free from the substance to be transferred into cells is electrosprayed thereon. Consequently, cells into which the substance to be transferred into cells has been transferred (Material A in Cell) can be obtained. The substance to be transferred into cells is transferred into cells by electrospraying a liquid free from the substance on cells that coexist with the substance. That is, the liquid is not intended to be transferred directly into the cells but is used to allow the substance to be taken up into the cells.

Figure 2:
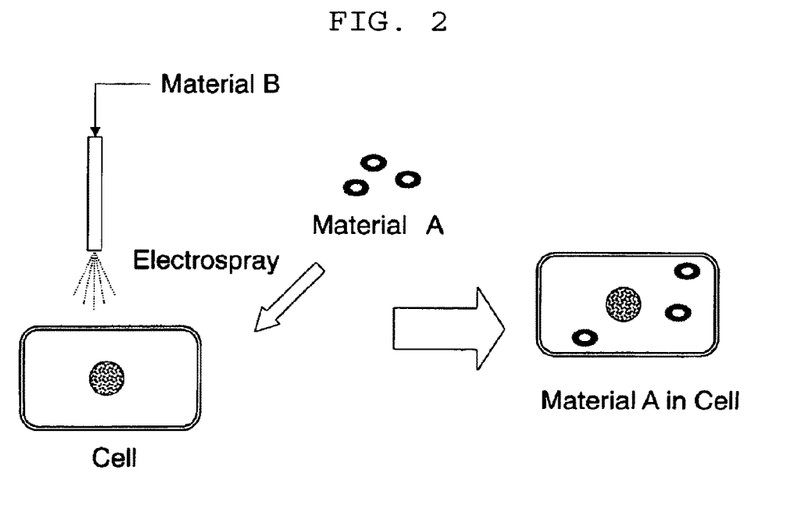
FIG. 2 is a schematic view showing a case in which electrospray is first performed, and then cells are brought into contact with a substance to be transferred into cells.

FIG. 2 shows another embodiment in which a liquid free from the substance to be transferred into cells is first electrosprayed on cells and then the cells are brought into contact with the substance to be transferred into cells.

In FIG. 2, cells (Cell) are sprayed with a liquid (Material B) free from the substance to be transferred into cells. Then, the substance to be transferred into cells is added. Consequently, the substance to be transferred into cells can be transferred into cells. The substance is more easily transferred when cells are brought into contact the substance within a shorter time after spraying. It depends on conditions and types of cells as well as spray conditions, but the cells are desirably brought into contact the substance within 30 minutes or less, preferably within 15 minutes or less, more preferably within 3 minutes or less. When the substance to be transferred into cells is brought into contact with cells, the substance is preferably in a form of solution, but may be in a form of powder or the like that contains the substance so long as the cells are not affected.

The voltage applied to the tube tip can be set to an optimum value which is obtained from the distance from cells, the tube size, the flow rate and properties of a liquid to be electrosprayed, and the like. The voltage is preferably in the range of 0.1 kV to 100 kV, more preferably in the range of 1 kV to 20 kV, in terms of a potential difference between the liquid at the tube tip and the cells. When the voltage is lower than 0.1 kV, transfer efficiency of the targeted substance into cells becomes lower. Furthermore, a voltage of higher than 100 kV is not preferable either because no significant improvement is expected in transfer efficiency of the substance into cells, but a risk of cell death is increased.

The inside diameter of the tube tip is preferably from 0.01 μm to 10 mm, more preferably from 1 μm to 5 mm. A tube tip which is smaller than 0.01 μm is not preferable because a very high pressure is required due to the too narrow flow channel. On the other hand, when the inside diameter is greater than 10 mm, a liquid sprayed is not converted into droplets, and thereby electrospray may not be generated.

The distance between the tube tip and cells is preferably 0.1 μm to 2000 mm when electrospray is performed. When the distance is shorter than this range, breakdown easily occurs. When the distance is longer than this range, the applied voltage becomes too high to be realistic. The distance is more preferably from 1 μm to 500 mm.

The amount of a liquid to be electrosprayed on cells can be changed depending on the amount, the type, and the shape of cells. Furthermore, electrospraying time is accordingly changed.

Specifically, for example, when adhesive animal cells on a petri dish having a diameter of 3.5 cm are electrosprayed, the amount of a liquid to be sprayed is preferably in the range of 1 μL to 4 mL, more preferably in the range of 10 μL to 2 mL.

Furthermore, when microorganism colonies on a petri dish having a diameter of 6 cm are electrosprayed, the amount of a liquid to be sprayed is preferably in the range of 1 μL to 8 mL, more preferably in the range of 10 μL to 4 mL.

To attain the object of the present invention, a liquid to be electrosprayed is required to contain no substance that adversely affects cells. As such a liquid, water or an aqueous solution is preferred. Water may be any of ion exchange water, distilled water, or sterilized water. Furthermore, the aqueous solution may contain metal ions, organic solvents, macromolecular compounds, media, buffer substances, and the like. As more specific examples of metal ions that can be contained in water, metal ions in groups I to XV in the periodic table are preferred, and metal ions in groups I to III or groups VI to XII are preferred. In particular, aqueous solutions of Li, Na, K, Cs, Mg, Ca, La, Cr, Mo, W, Mn, Fe, Co, Ni, Cu, and Zn ions, which are often used in biochemical experiments, are easy to use. These metal ions may be supplied in any form of halides, organic acid salts, phosphates, nitrates, sulfates, borates, carbonates, silicates, and so forth.

Examples of organic solvents that can be contained in a liquid to be electrosprayed include methanol, ethanol, propanol, butanol, ethylene glycol, propylene glycol, glycerine, polyethylene glycol, polypropylene glycol, acetone, methyl ethyl ketone, ethyl acetate, dimethyl sulfoxide, sulfolane, ethanolamine, diethanolamine, triethanolamine, propanolamine, dipropanolamine, tripropanolamine, chloroform, methylene chloride, acetamide, methylacetamide, dimethylacetamide, N-methylpyrrolidone, formamide, methylformamide, dimethylformamide, polyethylenimine, polyallylamine, hexane, triacetin, and so forth.

Examples of macromolecular compounds that can be used include polyethylenimine, polyallylamine, polyethylene glycol, polyvinyl alcohol, spermidine, agarose, starch, cellulose, polyvinylpyrrolidone, alginic acid, carrageenan, and so forth.

Examples of media that can be contained in a liquid to be sprayed include LB medium, Sauton's medium, SOB medium, Ham's medium, Eagle's medium, modified Eagle's medium, RPMI medium, Fisher's medium, MCDB medium, white's medium, and Murashige and Skoog medium. In addition to these, amino acids, sucrose, sorbitol, peptone, yeast extract, surfactants, serum, and the like may be contained as medium components.

As equilibrated buffers, mixtures used in biochemical experiments such as EDTA aqueous solution, tris(hydroxymethyl)aminomethane hydrochloride buffer (tris buffer), tris-EDTA buffer (TE buffer), phosphate buffer (PBS), tris-acetic acid-EDTA buffer (TAE buffer), Hanks' balanced salt solution (HBSS), and Eagle's balanced salt solution (EBSS) can be used.

Concentrations of the aqueous solution to be used in the present invention are not particularly limited. However, the concentration should be adjusted if the solution has an osmotic pressure which is so different from that of cells in use as to have adverse effects thereon. Furthermore, to improve transfer efficiency, it is preferable that gene transfer reagents such as liposomes and basic polymers that can be generally used for target cells are allowed to coexist.

The substance to be transferred into cells in the present invention is not particularly limited, and particularly useful examples thereof are genes. Specific examples include DNA, RNA, and similar compounds or derivatives thereof. These are supplied in the forms of plasmids, phages, viruses, viroids, oligo DNA, oligo RNA, micro RNA, and the like. Sizes of nucleotide sequences are not particularly limited. Nucleotides may be either double-stranded or single-stranded.

Furthermore, in general, substances smaller than genes can be more easily transferred in the present invention. Examples of such substances include proteins, peptides, sugars, lipids, agricultural chemicals, antibacterial agents, metal ions, fluorescence-labeled reagents, isotope-labeled reagents, and so forth.

The mechanism by which a substance is transferred into cells by the method of the present invention is uncertain but is anticipated as follows. When a liquid becomes in a state of electrospray, a large amount of minute charged droplets are generated. These are sprayed to bombard cells. As a result, the electric field is unbalanced between the inside and the outside of cells so as to generate pores in the cell membrane, and then the substance that exists in the vicinity of these pores is considered to be taken up into cells through the pores. It is considered that these pores start to close after electrospraying, and are restored in about 30 minutes.

The liquid can be sprayed under an atmosphere of a gas that has no fatal action on cells or danger of explosion, such as air, nitrogen, carbon dioxide, argon, and SF6. In this sense, air and nitrogen are commonly used and can be easily used.

Pressure is not particularly limited so long as cells can be treated without killing them, and the range from 1 pa to 1 Mpa is easily used. Atmospheric pressure is particularly easily used.

To prevent contamination such as incorporation of other microorganisms, it is very important to conduct spraying under an antiseptic condition. Specifically, contamination can be prevented by spraying inside a case or by use of a clean booth or the like. Furthermore, since a liquid can be sprayed in the opposite direction to gravity by this method, cells may be placed in an upper position to prevent incorporation of the falling contamination source when spraying is conducted.

The temperature during electrospraying is not particularly limited. Any temperature at which cells do not die can be used, and room temperature is easily used.

Figure 3:
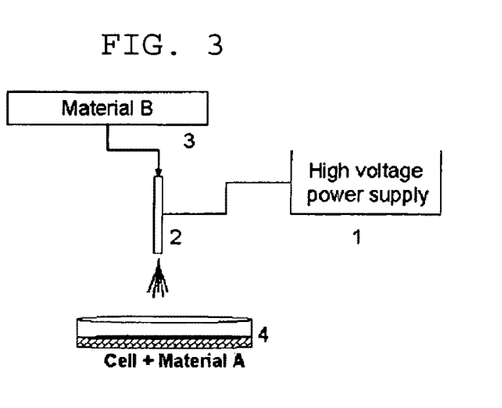
FIG. 3 is a schematic view of an apparatus for transferring a substance into cells.
Figure 4:
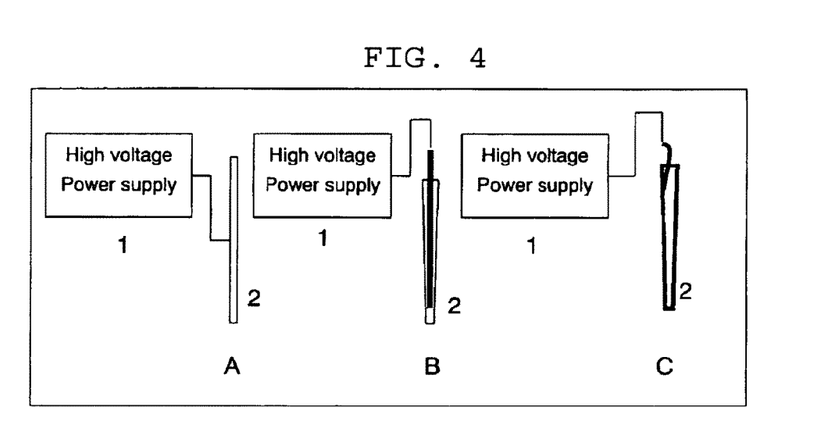
FIG. 4 is a schematic view of tubes for an apparatus for transferring a substance into cells.
Figure 5:
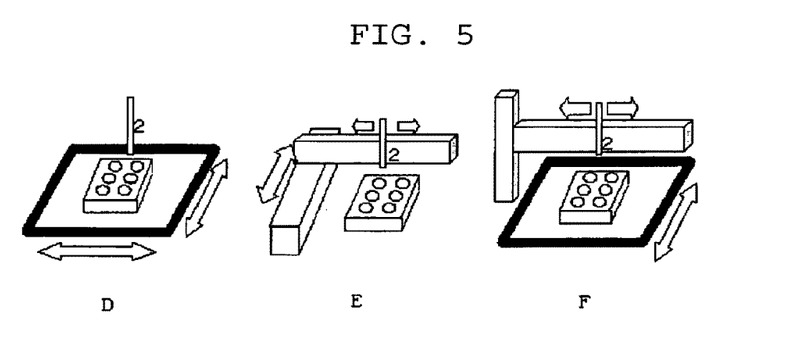
FIG. 5 is a schematic view of apparatuses for transferring a substance into cells, which has a movement mechanism.

FIG. 3 shows a schematic structure of an apparatus for transferring a substance into cells by the present method for transferring a substance into cells, in which electrospray is performed in the coexistence of cells and the substance to be transferred into cells.

The apparatus is composed of a high voltage power supply 1, a tube 2, a liquid (Material B) 3, and cells and a substance to be transferred into cells (Cell+Material A) 4. The liquid 3 to which a voltage is applied is sprayed through the tube 2 on cells and the substance to be transferred into cells 4. At this time, a voltage is applied to the liquid 3 by the high voltage power supply 1. Consequently, the liquid 3 is charged and sprayed from the tube 2 on cells and the substance to be transferred into cells 4. Referring to the mechanism more specifically, the high voltage power supply 1 for applying a voltage to the liquid 3 is connected to the tube 2 via a cable or the like. Furthermore, the tube is located at a position where cells and the substance to be transferred into cells 4 can be sprayed.

The liquid is charged and converted to droplets at the tube tip to which a voltage is applied by the high voltage power supply to generate a state of electrospray. When the voltage is applied, repulsion of electric charge on the surfaces of droplets becomes greater than the surface tension of droplets, droplets are made minute, and charged droplets are sprayed on cells at a high speed due to the electric field. Since formation of electrospray varies depending on the voltage, the distances from cells, the tube size, the flow rate of the liquid, the properties of the liquid, and the like, the apparatus has a structure which can be adjusted suitably depending on purposes.

This apparatus has a pump so that the liquid can be quantitatively fed to the tube. If the apparatus has no pump, the material is fed to the tube utilizing gravity or pressure. In contrast, the pump makes it possible to quantitatively feed the liquid more easily. As the pump, a tube pump, plunger-pump, diaphragm pump, syringe pump, or the like can be used, and one may be selected therefrom depending on purposes.

The structure of the apparatus will be more specifically explained. The high voltage power supply generates a potential difference between the liquid to be sprayed and target cells. In the present invention, the amount of electric current that flows is little, and is not particularly limited. 1 mA or lower is sufficient. The high voltage power supply and the tube are connected together. They can be connected via a high voltage cable.

The voltage applied to the liquid to be sprayed may be either positive or negative. In the present invention, spraying droplets onto cells may be accompanied with electric discharge, but naturally electric discharge lasting so long as to damage cells is not preferable.

The material of the tube may be metal, plastic, glass, ceramic or the like, and is not particularly limited. However, when a tube made of a nonconductive material is used, a tube provided therein with an electrode contacting the liquid or a tube coated with a conductive substance on the surface thereof needs to be used. FIG. 4 schematically shows examples of connection between the tube and the high voltage power supply.

When a conductive material such as metal is used for a tube as shown in A, an electrode is connected to the tube so that a liquid fed therein can be charged. B shows the case where an insulator such as glass is used for a tube. In this case, a conductive electrode such as of metal is placed therein to charge the liquid. C shows the case where the inside of the electrode is coated with a conductive substance, and the inside of the tube is connected to the high voltage power supply to charge the liquid.

The shape of the tube tip may be not only straight but also may be tapered, but is not particularly limited. Furthermore, the tube may have a double-tube structure, and a gas may be fed together with the liquid. As the tube, an electrospray tube used for mass spectrometry or the like may be used. Furthermore, a nanospray that can feed a trace amount of liquid can be used so long as transfer efficiency of a substance to be transferred into cells dose not decrease.

At least one tube is sufficient for spraying, but multiple tubes make it possible to spray the liquid on surfaces of cells more widely, and further make it possible to treat multiple specimens at the same time.

The container in which cells are placed together with a substance to be transferred into cells is not particularly limited so long as it can receive the liquid sprayed from the tube, and this is applicable when spraying is performed on aggregates of cells such as colonies, tissues, and individual organisms. For example, when cells are targeted, containers such as petri dishes and test tubes are easy to use.

To spray the liquid so as to efficiently transfer the substance into cells, connection to ground can be made to eliminate electrostatic charge so that a potential difference between cells and the container can be obtained within a preferable range. Specifically, when spraying is performed on cells which are placed in a petri dish together with a substance to be transferred into the cells, it is preferable that the cells are connected to ground via a solution or a gel which contacts the cells in the petri dish. No problem arises even if cells are placed and moved on a stage that can be rotated or positioned so that cells can receive the spray of liquid droplets uniformly.

If the apparatus is provided with an electromagnetic optical system, the location of the spray and the extent of area on which droplets are sprayed can be controlled. For example, droplets can be sprayed on a more localized area by placing a component having functions of a mask, a lens and a collimator upstream of the area on which spraying is performed. Furthermore, a quadrupole lens or the like enables positioning, scanning and the like of the spray. For the mask function, a plate-like (film) element made of an organic polymer material, metal or ceramic can be used to determine a spray range. Furthermore, a charged metal mask or dielectric mask element can be used for lens and collimator functions.

In the present invention, the liquid to be electrosprayed does not have to be changed but may be the same liquid even when the type of cells or the substance to be transferred is changed. Therefore, for example, different substances can be continuously transferred into different cells in each well using a container such as a 96-well microplate. For example, if different cells are placed together with different genes in each well, efficient gene transfer can be performed in a short time.

Specifically, for example, a large number of samples can be continuously treated by attaching an electrospray tube to an arm that can move in the XY directions. Alternatively, cells can be placed and moved on an XY stage so that cells can be moved. Furthermore, a combination of a tube moving along the X axis and a stage moving along the Y axis can be used. The movement mechanism may be either an XY type or a scalar type, and any of electric, air or human power can be used as a power for this movement. These may be further provided with a mechanical position control function so that automation and labor-saving of operations may be achieved.

FIG. 5 shows specific movement mechanisms. D is a mechanism whose stage moves in XY directions. E is a mechanism whose tube moves in XY directions. F is a mechanism whose tube moves in the X direction, and whose stage moves in the Y direction.

According to the present invention, types of substances to be transferred into cells or cells to be targeted for the transfer can be changed without the need of changing the liquid to be electrosprayed. Furthermore, such a change can be efficiently made by employing the above-mentioned mechanisms. Furthermore, even when cells are changed, the liquid to be electrosprayed does not have to be changed so that the transfer can be achieved efficiently. Furthermore, since the main consumable material in the present invention is the liquid to be electrosprayed, which may be water, the transfer of substances can be conducted at very low cost.

Furthermore, no complex procedure is required, and biochemically significant substances such as genes can be easily transferred into cells only by electrospraying a liquid and bringing cells into contact with a substance to be transferred into cells. Furthermore, procedures such as removal of media used for cell culture or washing of cells with washing agents may be optionally added before electrospray is performed.

Hereinafter, the present invention will be explained more specifically by way of examples and comparative examples. However, the present invention is not limited to these examples.

EXAMPLE I-1

1. Experimental Apparatus

Figure 6:
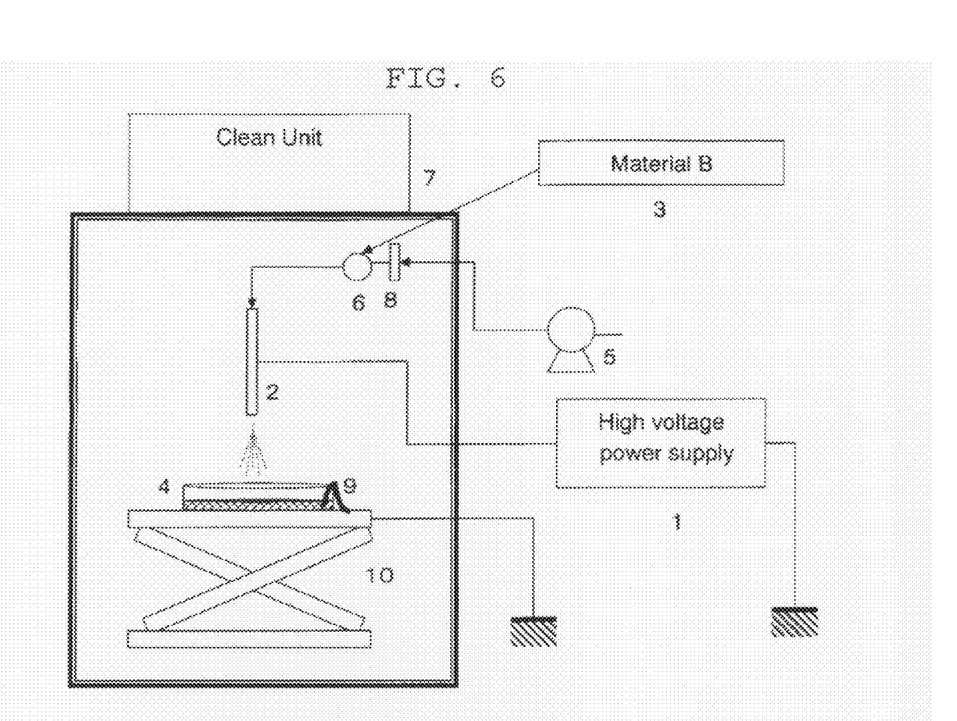
FIG. 6 is a view of an apparatus for transferring a substance into cells, which was used in experiments.

The apparatus used in the experiment is shown in FIG. 6.

A high voltage power supply 1 is connected to a tube 2 via a high voltage cable and further connected to ground. The tube 2 is made of stainless steel and of a luer lock type having an outside diameter of 0.36 mm and an inside diameter of 0.18 mm. This is connected to a sample injection port 6. A liquid 3 to be sprayed is transferred from this sample injection port. A pump 5 is a tube pump which feeds air. The liquid 3 to be charged is pushed to the tube by this air pressure. At this time, air is supplied through a filter 8 made of cellulose acetate. Animal cells and a substance to be transferred into cells 4 are placed on a 60-mm polystyrene petri dish. The petri dish is set on a jack 10. The jack is connected to ground. The inside of the petri dish is connected to the jack via a stainless-steel ribbon 9 so that the inside is connected to ground. The portion to be sprayed is set in an acrylic container with an aluminum frame having an internal size of 272×260×370 mm, and an HEPA clean unit 7 that blasts out in an amount of 0.5 m³/min at a speed of approx. 0.25 m/s is set on top of the container. Clean air flows downwards from the top, and an outlet is provided at the bottom of the container.

2. Transfer of Gene into Animal Cells

The above-mentioned apparatus 1 was used as an experiment apparatus.

A plasmid (4.7 kbp) incorporated with a green fluorescence protein (GFP) gene was used as a substance to be transferred into cells. Fibroblasts (CHO cells) established from Chinese hamster ovary on biopsy were used as cells. CHO cells were seeded on a 35-mm dish at a concentration of $1.0 \times 10^4$ and cultured in a medium composed of α-MEM medium+10% FBS in a $CO_2$ incubator at 37° C. for four days. The medium for cells was removed, and 100 μL of the plasmid having a concentration of 50 μg/mL was added thereto.

100 μL of water was sprayed at a distance of 2 cm from the tube tip to the jack. At this time, −7 kV was applied to the tube. Water in the form of electrospray was sprayed from the tube on animal cells in the petri dish. After spraying, the medium was placed in the petri dish and further cultured for four days.

Figure 7:
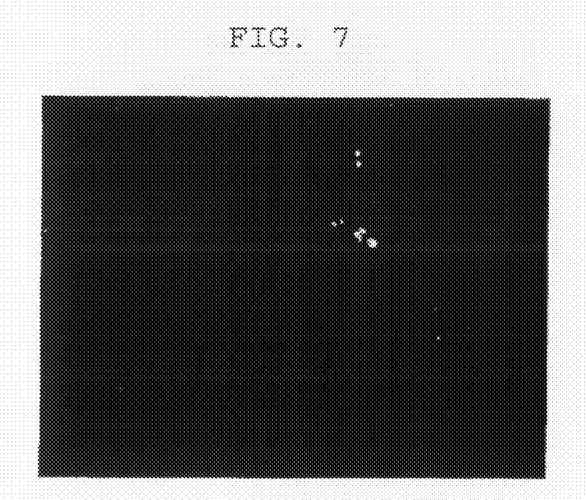
FIG. 7 is a photograph of fluorescence microscopy, showing CHO cells into which the GFP gene was introduced.

Transfer of the gene was confirmed by observation of cells showing green fluorescence with a fluorescence microscope. FIG. 7 shows a photograph of fluorescence microscopy of CHO cells into which the GFP gene was transferred.

EXAMPLE I-2

Experiment was performed in the same manner as in Example I-1 except that the spraying of 100 μL of water was carried out after 400 μL of the medium was further added to the cells and plasmid solution. At this time, −7 kV was applied to the tube. As a result, transfer of the gene was confirmed by observation of cells showing green fluorescence with a fluorescence microscope.

EXAMPLE I-3

Experiment was performed in the same manner as in Example I-1 except that a voltage of −10 kV was applied to the tube. As a result, transfer of the gene was confirmed by observation of cells showing green fluorescence with a fluorescence microscope.

EXAMPLE I-4

Experiment was performed in the same manner as in Example I-1 except that 100 μL of water was sprayed onto cells without addition of the plasmid. At this time, −7 kV was applied to the tube, and a plasmid solution was added one minute after spraying. As a result, transfer of the gene was confirmed by observation of cells showing green fluorescence with a fluorescence microscope.

EXAMPLE I-5

Experiment was performed in the same manner as in Example I-1. However, a 24-well polystyrene plate was used as a container, and each well was connected to a metal ground wire. A voltage of −10 kV was applied to the tube. As a result, transfer of the gene was confirmed in every well by observation of cells showing green fluorescence with a fluorescence microscope.

COMPARATIVE EXAMPLE I-1

Experiment was performed in the same manner as in Example I-1 except that electrospray was not performed after mixing the plasmid. After cultured, cells were observed with a fluorescence microscope, but cells did not show any fluorescence, that is, the gene failed to be transferred.

EXAMPLE II-1

1. Experimental Apparatus

The apparatus used in the experiment is shown in FIG. 6. A high voltage power supply 1 is connected to a tube 2 via a high voltage cable and further connected to ground. The tube 2 is made of stainless steel and of a luer lock type having an outside diameter of 0.36 mm and an inside diameter of 0.18 mm. This is connected to a sample injection port 6. A liquid 3 to be sprayed is transferred from this sample injection port. A pump 5 is a tube pump which feeds air. The liquid 3 to be charged is pushed to the tube by this air pressure. At this time, air is supplied through a filter 8 made of cellulose acetate. The high voltage power supply 1 to be used is provided with a circuit breaker and has a current limit of 1 mA. Cells and a substance to be transferred into cells 4 are placed on a 60-mm polystyrene petri dish. The petri dish is set on a jack 10. The jack is connected to ground. The inside of the petri dish is connected to the jack via a stainless-steel ribbon 9 so that the inside is connected to ground. The portion to be sprayed is set in an acrylic container with an aluminum frame having an internal size of 272×260×370 mm, and an HEPA clean unit 7 that blasts out in an amount of 0.5 m$^3$/min at a speed of approx. 0.25 m/s is set on top of the container. Clean air flows downwards from the top, and an outlet is provided at the bottom of the container.

2. Experiment of Transferring a Substance into Cells 1.5% agarose-B medium was placed in a polystyrene petri dish having a diameter of 6 cm, and *Escherichia coli* HB101 strain was seeded all over the petri dish and cultured at 25° C. for two days to grow colonies all over the petri dish.

100 μL of a TE buffer solution (105 μg/mL) of a plasmid pUC19 having an ampicillin resistance gene was added to this medium. Then, by way of a stainless-steel ribbon, the agar medium in the petri dish was connected to ground, and 100 μL of water was sprayed on *Escherichia coli* colonies from the height of 2.5 cm. At this time, −7 kV was applied to the tube.

After spraying, colony cells in the petri dish were scraped, added to the LB medium, and centrifuged. The obtained precipitates of bacterial cells were seeded on a 1.5% agarose-LB medium containing ampicillin and cultured at 30° C. for two days. As a result, colonies were grown, showing that *Escherichia coli* had acquired ampicillin resistance.

EXAMPLE II-2

The same procedures as in Example II-1 were repeated except that a voltage of −18 kV was applied during spraying. The obtained centrifuged bacterial cells were seeded on a 1.5% agarose-LB medium containing ampicillin and cultured at 30° C. for two days. As a result, colonies were grown, showing that *Escherichia coli* had acquired ampicillin resistance.

EXAMPLE II-3

Electrophoresis Experiment

Plasmids were collected from ampicillin-resistant *Escherichia coli* obtained in Examples II-1 and II-2 and the HB101 strain subjected to spraying, using a plasmid purification kit made by QIAGEN, and then subjected to electrophoresis on an agarose gel.

Figure 8:
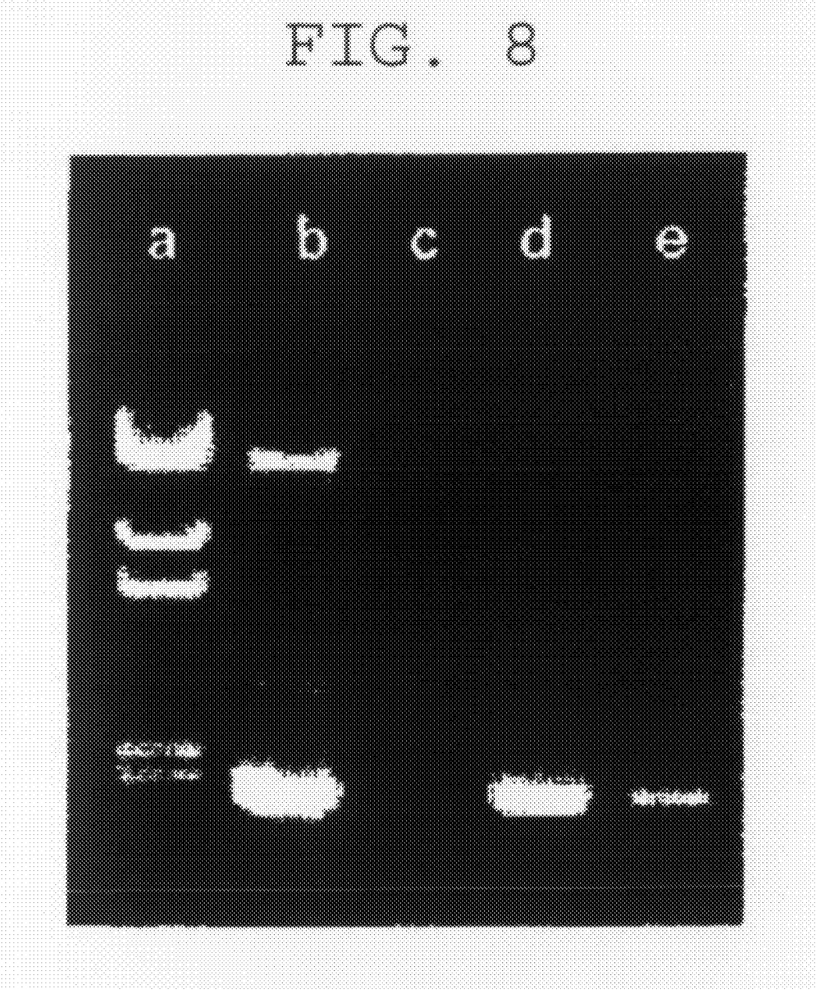
FIG. 8 is a photograph of electrophoresis, showing plasmids of ampicillin resistant strains.

As a result, plasmids of the ampicillin-resistant strains obtained in Examples II-1 and II-2 migrated to the same electrophoretic position as that of pUC19 used for gene transfer, showing that the substance to be transferred into cells had been transferred into cells by using the method of the present invention. No plasmid was observed in the HB101 strain (FIG. 8).

EXAMPLE II-4

The nozzle portion of a small-sized dispenser robot equipped with a mechanism for movement of the spray position was replaced with an electrospray tube. This robot has a mechanism that can change the position of the nozzle in the X-axis direction and the stage in the Y-axis direction, so that spray can be done while controlling the position two-dimensionally. A ground was attached to a chip-like plate having four wells using a metal wire, and spraying was performed. All the four wells were sprayed by moving the spray tube.

COMPARATIVE EXAMPLE II-1

The same procedures as in Example II-1 were repeated except that spraying was not performed. The obtained centrifuged bacterial cells were seeded on a 1.5% agarose-LB medium containing ampicillin and cultured at 30° C. for two days. As a result, no colony was grown.

COMPARATIVE EXAMPLE II-2

The same procedures as in Example II-1 were repeated except that no voltage was applied during spraying. The obtained centrifuged bacterial cells were seeded on a 1.5% agarose-LB medium containing ampicillin and cultured at 30° C. for two days. As a result, no colony was grown.

EXAMPLE III-1

Example of Transfer of Gene into Chicken Embryo

1. Experimental Apparatus

Figure 9:
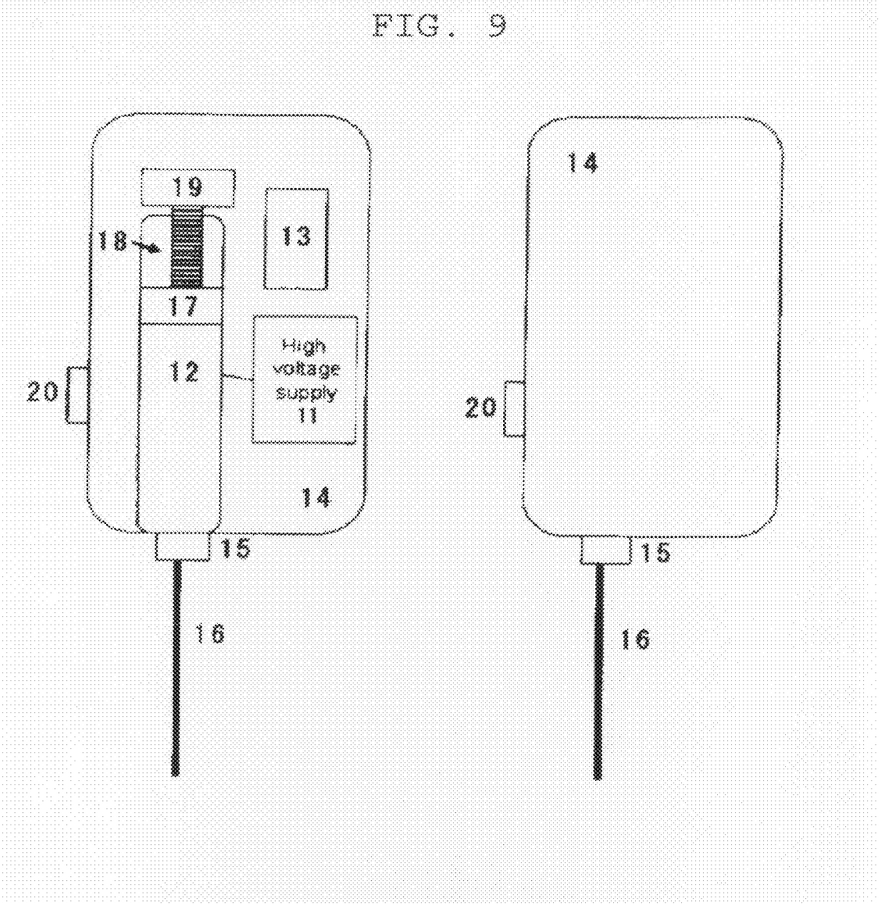
FIG. 9 is a schematic view of an apparatus for transferring a substances into cells, which was used in Example III-1.

The electrospray apparatus used in the experiment is shown in FIG. 9. In the apparatus in FIG. 9, a dry-cell battery is used as a power supply 13 to supply 3 V. This 3 V is converted to +10 kV by a voltage booster circuit 11 to connect with a tank 12. The tank 12 is made of conductive plastic, but is covered with an insulating plastic except the portion contacting a high voltage. The capacity of the tank is approx. 10 mL. A cylinder 17 is provided inside, and when a shaft 18 is rotated by a motor 19, a liquid in the tank is transferred to a stainless-steel tube 16 which has an inside diameter 0.1 mm and has a luer lock connected to a luer lock-type joint 15. The supply speed of the liquid to be sprayed from the tube is 120 μL/min. In this apparatus, the voltage booster circuit 11, the tank 12, the power supply 13, the cylinder 17, the shaft 18, and the motor 19 are housed in an apparatus casing 14, and spraying is operated by a switch 20 provided on the outer side surface of the apparatus casing 14.

2. Experiment of Gene Transfer into Chicken Embryo

The phosphate buffer (PBS) used in the experiment was a solution of pH 7.3 composed of 8 g/L of NaCl, 0.2 g/L of KCl, 2.9 g/L of NaHPO$_4$.12H$_2$O, and 0.2 g/L of KH$_2$PO$_4$.

Figure 10:
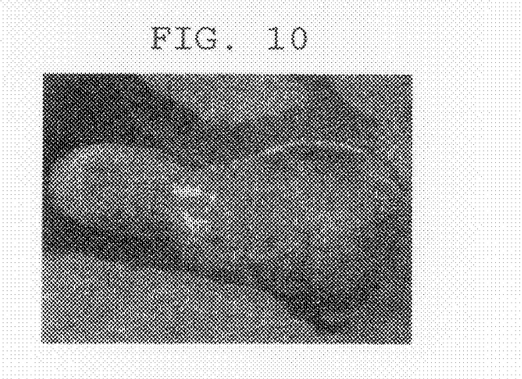
FIG. 10 is a photograph of fluorescence stereoscopic microscopy, showing chicken embryo into which the GFP gene was introduced.

One and a half days after the start of incubation of eggs (37.8° C.), chicken embryos were removed and placed on a mixed medium of egg white and agar. 0.1 μL of a solution of a plasmid (4.7 kba) incorporated with a green fluorescence protein (GEP) gene colored by 2% Fast Green in the above-mentioned PBS at a concentration of 4.3 μg/μL was added dropwise to a targeted region. After 30 seconds, the above-mentioned PBS was electrosprayed using the above-mentioned electrospray apparatus from the height of 10 cm for 15 seconds, while monitoring by microscopy. Cells were incubated at 37.8° C. and observed with a fluorescence stereoscopic microscope on the following day. The results are shown in FIG. 10. In FIG. 10, expression of GFP was observed in a 1-mm region of the full-length 6 to 7 mm, and it was confirmed that the gene had been transferred.

DESCRIPTION OF SYMBOLS

Material A: the substance to be transferred into cells.
Material B: the liquid free from the substance to be transferred into cells.
Material A in Cell: cells into which the substance to be transferred into cells has been transferred.
1: High voltage power supply.
2: Tube.
3: The liquid free from the substance to be transferred into cells (Material B).
4: Cells (Cell) and the substance to be transferred into cells (Material A).
5: Tube pump.
6: Liquid (Material B) injection port.
7: Clean unit.
8: Cellulose acetate filter.
9: Stainless-steel ribbon for grounding.
10: Jack.
11: Voltage booster circuit.
12: Tank.
13: Power supply.
14: Apparatus casing.
15: Luer lock type joint.
16: Tube.
17: Cylinder.
18: Shaft.
19: Motor.
20: Switch.
A: A case where a conductive material is used for the tube.
B: A case where an insulator such as glass is used.
C: A case where the inside of an electrode is coated with a conductive material.
D: A case where the apparatus has a mechanism for moving the stage in XY directions.
E: A case where the apparatus has a mechanism for moving the tube in XY directions.
F: A case where the apparatus has a mechanism for moving the tube in X direction and the stage in Y direction.
Lane a: Size marker.
Lane b: pUC19.
Lane c: HB101 strain.
Lane d: Example II-1.
Lane e: Example II-2.

The invention claimed is:

1. A method for transferring a substance into cells, which comprises either:
    (a) electrospraying a liquid free from the substance to be transferred into cells so that droplets consisting essentially of said liquid are generated and brought into contact with cells whilst said cells are brought into contact with the substance to be transferred into the cells, or
    (b) electrospraying a liquid free from the substance to be transferred into cells so that droplets are generated and first brought into contact with cells and then bringing said cells into contact with the substance to be transferred into said cells.

2. The method for transferring a substance into cells according to claim 1, wherein in (b) said cells are brought into contact with the substance to be transferred into cells within 30 minutes or less after said droplets have been brought into contact with said cells.

3. The method for transferring a substance into cells according to claim 1, wherein a potential difference between the liquid and the cells is 0.1 kV to 100 kV.

4. The method for transferring a substance into cells according to claim 1, wherein the liquid which is electrosprayed is water that is free from the substance to be transferred into cells or an aqueous solution that is free from the substance to be transferred into cells.

5. The method for transferring a substance into cells according to claim 1, wherein the substance to be transferred into cells is a gene.

* * * * *